United States Patent [19]

Berns

[11] Patent Number: 5,365,624

[45] Date of Patent: Nov. 22, 1994

[54] APPARATUS FOR AUTOMATIC AND SIMULTANEOUS CARING FOR TEETH AND GUMS

[76] Inventor: Michael S. Berns, Apt. 270866 Isabella St., Toronto, Ontario, Canada, M4Y 1N3

[21] Appl. No.: 25,277

[22] Filed: Mar. 2, 1993

[51] Int. Cl.⁵ .............................................. A61C 17/38
[52] U.S. Cl. ..................................... 15/22.1; 601/129
[58] Field of Search ............................. 15/22.1, 22.2; 128/62 A

[56] References Cited

U.S. PATENT DOCUMENTS

| | | | |
|---|---|---|---|
| 4,011,616 | 3/1977 | Kennedy | 15/22.1 |
| 4,225,710 | 9/1980 | Solow | 15/22.1 |
| 4,795,347 | 1/1989 | Maurer | 15/22.1 |

Primary Examiner—Edward L. Roberts
Attorney, Agent, or Firm—Bauer & Schaffer

[57] ABSTRACT

A safe, hygienic and effective device for caring for the interior of the mouth is presented. The system includes easily interchangeable accessories for a brushing device that allows it to function also as a polisher, washer, massager/stimulator, oral irrigator, oral syringe, lubricator, and protector of the teeth and gums. In the example presented, water-driven motors housed inside flexible material formed so that it is capable of fitting comfortably inside the human mouth drive heads in an up-and-down or rotating motion that brush or polish or massage/stimulate or irrigate the interior and exterior of all teeth, top and bottom, and gums, simultaneously, while also supplying fresh-water lubrication and paste or polish or mouthwash or the like and also removing exhaust fluids and exhaust substances from the mouth by a vacuum/suction or pressure or gravity action. A controller at the water supply monitors the duration of use, direction of fresh water flow, and water temperature and water pressure, and controls the direction of fresh water flow to none or one or more of the mouth care devices simultaneously from each water supply source; portable adapters are available. Timers and automatic safety shut-offs prevent injury from excessive use or in the event the fresh water temperatures or pressures from the water supply are above or below pre-set or user-set levels. Another embodiment provides for using the device as a mouth protector or thumb-sucking inhibitor.

11 Claims, 7 Drawing Sheets

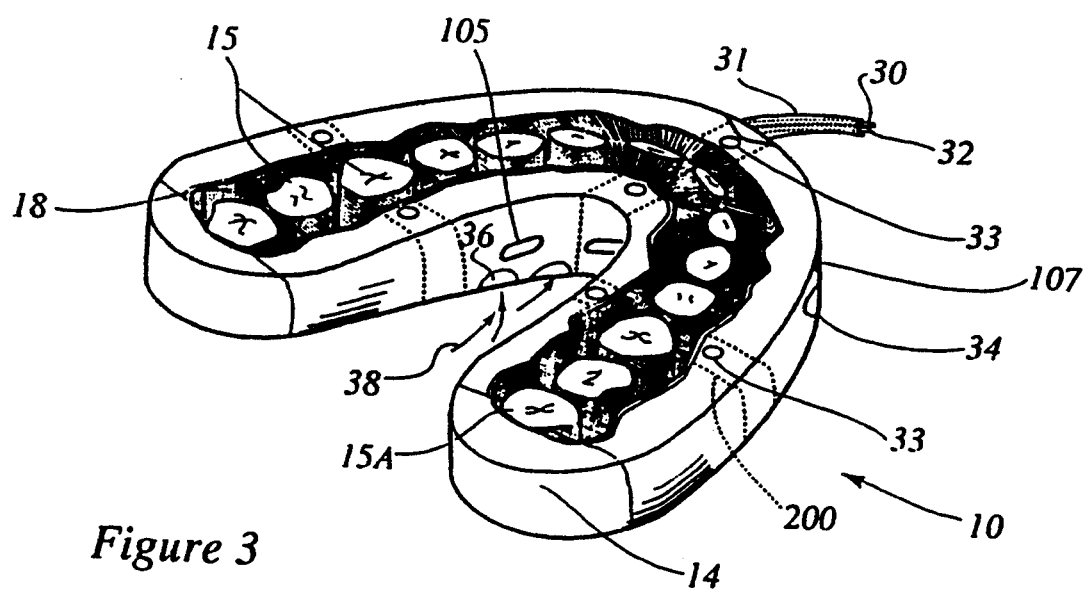
*Figure 3*
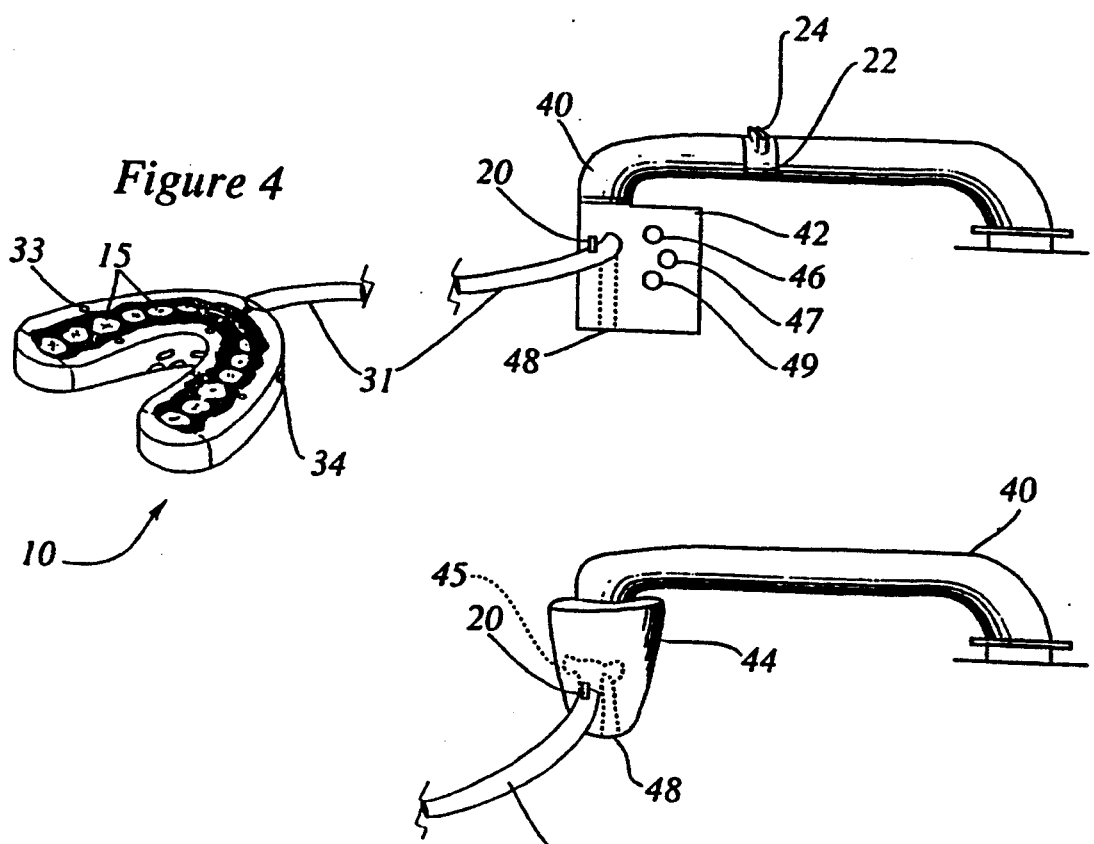
*Figure 4*
*Figure 4A*

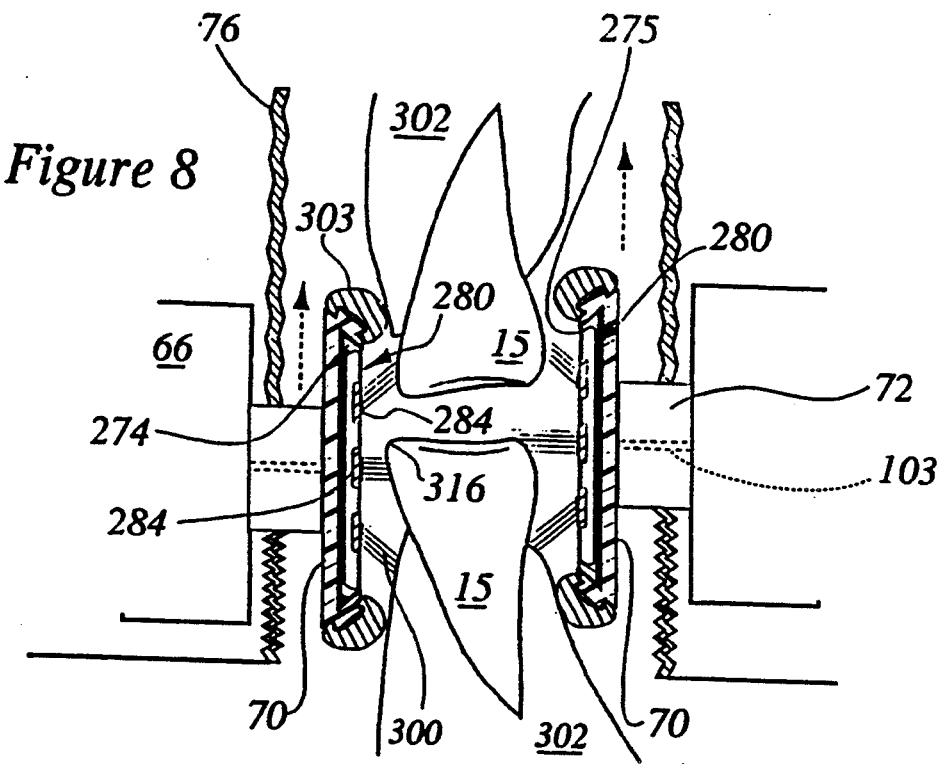
Figure 8
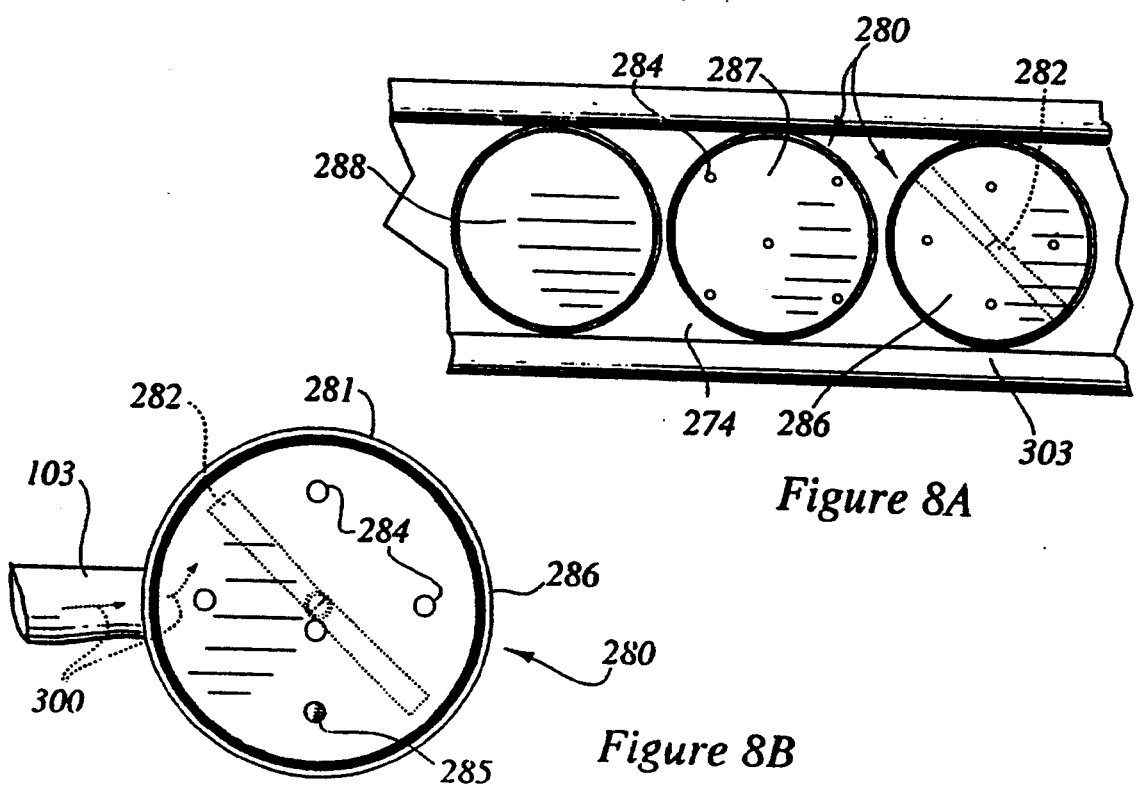
Figure 8A
Figure 8B

APPARATUS FOR AUTOMATIC AND SIMULTANEOUS CARING FOR TEETH AND GUMS

INTRODUCTION AND DESCRIPTION OF THE PRIOR ART

Over the last thirty to forty years a diverse array of manual and electric toothbrushes, oral irrigators, and flossers have enjoyed widespread commercial success. This attests to the important basic need to clean the teeth, gums, and whole mouth area: a need made recently more acute by the introduction of refined sugars in many commercial and home-prepared foods. The human organism (fortunately or unfortunately) evolves physically at a much slower rate than socially, and no biological mechanism yet exists to deal with this onslaught; hence the particular importance of such cleaning devices.

Nonetheless, many problems exist with these devices, and for many people and in many situations they are inadequate or unsuitable. Manual brushes, for instance, require the user to have a moderate degree of manual dexterity (at least) and the ability to firmly grasp the brush while moving it against the dental surfaces. The tiresomeness, difficulty and repetitiveness of manual brushing leads many to do less than is necessary; as is reported in *Consumer Reports*, September 1992, page 611: "People tend to brush for less than a minute. You need two or three minutes of manual brushing to do the job right," and so some teeth and gum surfaces may receive inadequate brushing or be missed altogether.

Electric toothbrushes, while requiring less physical effort, present the possibility of leakage and can pose an electrical hazard. They are more complicated than manual brushes and require more time in maintenance. Brushing too vigorously with electric brushes can irritate the gums or cause them to bleed excessively, possibly injuring the gums or eventually causing them to receded. Bleeding can spread oral bacteria to the bloodstream, a risk for users with various health conditions including heart and immunity problems. Because of these problems, children must often be supervised when using electric toothbrushes, and children under the age of ten probably should not use them at all.

Oral irrigators (pulsating jets of pressurized water) and oral syringes (non-pulsating jets of pressurized water), while of benefit to users with crowns, implants, braces, or non-removable bridgework (for whom flossing or brushing is impractical or not possible), can damage a user's cheeks and tongue if the lowest pressure settings are not used; this is particularly a problem for an unsuspecting adult, teen or child if there is no safety mechanism to prevent higher pressure settings from remaining after a particular user has finished with the tool.

Finally, flossing needs only be mentioned to note that it has found its best use as a cumbersome and sometimes painful way to remedy some of the deficiencies found in the other methods, particularly brushing.

However, it can be appreciated that none of the methods is all of: simple and safe to operate; hygienic, comfortable and effective to use; easy and inexpensive to maintain; and cost-effective to purchase, for most people in most situations. Thus, there is a need for such a device. The present invention fills this need by overcoming the foregoing deficiencies.

Although a large number of forms of the preceding tools have been entered into the patent literature in past years, virtually all of them fall prey to the deficiencies noted (or others peculiar to them) and need not be examined in detail here. One of some interest is U.S. Pat. No. 4,224,710, Solow, in which between 64 and 92 individual brushes mounted in a mouthpiece are "jackhammered" at an oblique angle against the sides of the tooth and the tooth-gum border. This device, while appearing visually in some ways superficially similar to the invention as it will be outlined later, falls prey to several substantial defects, including: (a) the undesirability of having only the one type of "jackhammer" movement at an acute angle to the tooth surface, when the up-and-down brush movement is the one recommended by professional dental practitioners; (b) unwieldiness and discomfort of a single piece of inflexible material being inserted into the mouth; (c) lack of a lubrication system to prevent dry-bristle damage to the teeth or gums; (d) probability of the extruding hinge mechanism in the back of the user's mouth causing the gagging reflex; (e) lack of provision for dental paste dispensing, which requires the user to somehow supply paste (evenly) to 64-to-92 brushes; (f) lack of provision for self-cleaning; (g) lack of provision for exhausting excess brushing fluids or substances; (h) lack of provision for storage when not i use; and (i) lack of provision for replacement or worn brushes. U.S. Pat. No. 4,538,315, Barth, incorporates a multiple-brush arrangement for a part of the mouth that improves on Solow at least by using more vertical and non-"jackhammer" type of motion of the bristles, which rotate against the sides, tops and bottoms of the teeth around an axis parallel to the gum arch. However, drawbacks (b), (c), (e), (f), (g), (h) and (i) remain undealt-with; and, as well, the interesting problem of how a curved axis can rotate while maintaining its orientation unchanged relative to the (of course nonrotating) gum arch is not explained.

The present invention will remedy all the mentioned failings of past devices and the failings of some others that will become clear as the invention is explained in more detail. With this new automated dental care device for the whole mouth, a safe, fast, comfortable, and effective means of dental care for people of all ages, including those with implants, crowns, braces, and bridgework, and people of limited dexterity, will be available for the first time.

Use is simple and convenient: in the preferred embodiment a flexible, lightweight and durable mouthpiece containing two rows of bristles, one inside and one outside the teeth, is inserted into the mouth. The mouth is clamped shut on the device, and power is supplied in the form of water from a bathroom faucet or other faucet. The water drives motors inside the device which principally function to automatically raise and lower the rows of bristles in a vertical motion, thereby brushing from above the gum-line all of the upper teeth to below the gum-line of all the lower teeth, and all the tooth surfaces in between. A second function of the motors is to automatically pressure- or vacuum-pump with gravity action the residual fluids and substances in the device and the residual mouth fluids and substances and expel them; a third function is to automatically supply fresh water in appropriate amounts as lubrication for the bristles; a fourth is to automatically drive the dispensers of toothpaste (or polish, or mouthwash, and so forth) which are placed within the motors.

In a second embodiment the motors also automatically drive the bristles up and down and simultaneously cause them to automatically rotate against all tooth and gum surfaces (which of course can be used for polishing all tooth surfaces, or enhance the tooth cleaning and gum massage action); in a third embodiment the motors automatically drive water out in pulsating or non-pulsating jets through small holes for oral irrigation or oral syringe of all teeth and gums. In all three embodiments, water temperature and strength, and, therefore, the brushing, irrigating, syringing, polishing, massaging, lubricating and paste dispensing actions of the present invention can be controlled by the temperature and pressure of the water entering from the faucet. In all three embodiments an optional controller or an optional connector at any faucet provides the user: (1) with means for monitoring the water pressure and temperature selection made by the user at the faucet, or (2) minimally, with built-in safety shut-offs which automatically stop the flow of water from the faucet to the device if pre-set (default) or user-set water pressure and temperature ranges are exceeded or when the pre-set (default) or user-set usage timer completes the allotted usage time. As well, multiple invented devices can be connected to and individually operated and monitored from one controller or one connector.

When not in use, the invented devices can be stored on the faucet with an attachment provides so as not to take up shelf or counter space.

A fourth embodiment entails having a cushioning piece in place of the brushes, and, optionally, another cushioning piece in place of the motors so the device may serve as a mouthguard in sports activities, or even as an anti-thumb-sucking device.

In all embodiments, the device will be very comfortable to wear and light in weight to use, easy and quick to insert and remove, and offer a stable and durable means when used for automatic dental hygiene, a mouthguard, or as a thumb-sucking inhibitor owing to: (1) its availability in various sizes (e.g., adult, teen or child), and (2) the flexibility, softness or elasticity of the outer material with an elastic positioning lock around the back teeth to make the outer material conform to the user's unique dentition and gums.

All embodiments are available in the one device: the reciprocating vertical brush with lubricating holes, the spinning bristles brush with lubricating holes, the unit with irrigation and syringe holes, and the cushioning piece, all fit into the same slot(s) and are quickly and easily removable and interchangeable.

In sum, then, the main advantages of this invention, relative to past examples of mouth care devices, are as follows: minimizing time and expense through simplicity of operation and small number of moving parts; ease of insertion, operation and removal; comfort of use (flexible, soft or elasticized material); the ability to automatically self-clean (simply by running when not in the mouth); small number of replaceable brushes (two or more in the first embodiment; individual brush-wheels pop out easily for replacement in the second embodiment); safe and easy to use for people of all ages and of all manner of dental and gum complexity; automatic shut-off safety features (pre-set default or user-set water temperature and pressure ranges, and pre-set default or user-set usage timer); the flexibility to have automatic and simultaneous brushing and massaging and lubricating of all teeth and gums (first embodiment), brushing and massaging and lubricating of all teeth and gums (second embodiment), polishing and lubricating of all teeth (second embodiment), or irrigating and massaging or syringing and massaging of all teeth and gums (third embodiment); the ability to have any type of paste, polish, or mouthwash evenly, simply, and automatically dispensed to all tooth surfaces; automatic clean-water lubrication of all teeth and gums; the automatic removal of waste fluids and substances from the user's mouth and the device; no chance of electric shock (no electricity is used to power the device); small size (invented device or multiple invented devices can store on faucet when not in use) and portability (when used with optional connector instead of controller, the device can be easily, quickly and temporarily attached to any faucet, such as in a hotel room, and then quickly and easily removed); safety and convenience through the use, for example, of clear material for the casing, so that cleanliness, amounts of dispenser paste and so on, and device operation can be accurately monitored (operation of the invented device's moving parts can also encourage user interest in dental hygiene and, therefore, help ensure regular use of the device to promote dental hygiene); ability to clean false teeth while in or outside the mouth, and in both cases in a way that is superior to overnight soaking in disinfecting solution( and thereby also avoiding the discoloration that occurs when the original teeth are brushed while the false teeth are cleaned in a different manner, for example, by soaking); ease of proximate storage and accessibility for use (on any faucet with the invented device(s) requiring no wall or counter storage space); and the ability to use the device as a teeth protector or thumb-sucking inhibitor (with breathing passages provided for all embodiments).

A main object of the present invention is to provide an apparatus for caring for the teeth and gums that includes at least brushing, cleaning, lubricating, massaging, irrigating, syringing, and polishing, comprising: (a) a housing of transparent or opaque flexible material, formed to follow the shape of a gum arch and fit on either side of the teeth; this housing having: (i) particularly flexible, expandable and compressible inner walls facing the teeth and gums; (ii) channels or tubes through the housing to conduct breathing air in and out of the mouth, fresh water into the housing and the mouth, and exhaust fluids and exhaust substances out of the mouth, such as used paste, polish, mouthwash, saliva, water, blood and the like; (iii) watertight covers on, or within, holes in the top surface of the housing; these holes being for the introduction of paste, polish, mouthwash, or the like into paste chambers inside the housing; (iv) flexible or soft surfaces on all external portions of the housings which come into contact with the mouth, teeth or gums; (v) one or more water-driven motors inside the housing; (vi) a bellows or vacuum chamber inside each motor to automatically suction exhaust fluids and exhaust substances away from the teeth and gums and out of the mouth, and a compression wall to assist in automatically propelling exhaust fluids and exhaust substances out of the housing; (vii) a paste chamber inside each motor; this paste chamber configured to be cyclically compressed by the compression wall and so automatically supply paste, polish, mouthwash or the like to the teeth and gums through a dispenser hole or holes in a housing inner wall; (viii) a bridge linkage connected to a rack in each motor through a housing inner wall and moving with a reciprocating vertical motion; the bridge integrally connected to a holder external to the housing; the holder having a head removeably attached and which moves up and down vertically with the linkage and the rack; (ix) means to connect the housing to a faucet to provide a flow of fresh water to the housing; and (x) means to monitor the fresh water temperature and pressure, including means to automatically shut off the flow of water to the housing when water temperature or pressure are unsafe.

It is also an object to provide such a device comprising:

(a) a housing of transparent or opaque flexible material formed to follow the unique shape of a user's dentition, gums and gum arch and fit comfortably on either side of the user's teeth and comfortably within the user's mouth; said housing comprising: (i) a flexible backmost portion fitting around the back of the backmost teeth; (ii) portals on the outer surface to conduct air to be breathed and carbon dioxide to be expelled by the user; (iii) portals on the outer surface to expel secondary exhaust fluids and exhaust substances; these fluids and substances to consist in used paste, polish, mouthwash, saliva, water, blood, and the like; (iv) portals on the inner surface, that is, the surface facing the tongue, to conduct clean air into the mouth and carbon dioxide and secondary exhaust fluids and substances into the housing; (v) channels or tubes through the housing to connect the portals appropriately; and (vi) pop-up or flush-fitting or recessed watertight covers on, or within, holes in the top surface of the housing for the introduction of paste, polish, mouthwash, or the like;

(b) a water-driven motor inside the housing, below each watertight cover; this motor to comprise: (i) a compression wall, oriented approximately horizontally; (ii) a nozzle emitting a high-speed fresh water jet at the underside of the compression wall, thereby driving it upwards; (iii) an upper secondary exhaust bellows chamber situated above the compression wall and being compressed as the wall rises; the upper chamber having on its bottom surface a one-way valve which opens downwards as the wall rises and the upper chamber is compressed thereby ejecting secondary exhaust fluids and exhaust substances from the upper chamber into a lower secondary exhaust bellows chamber; (iv) a paste chamber for paste, polish, mouthwash, or the like situated above the compression wall and being compressed as the compression wall rises; the paste chamber having a dispenser hole or holes opening towards the teeth, so that contents of the chamber are expelled towards the teeth as the compression wall rises; the paste chamber also having visible indicator markings on a wall to show amount of the contents remaining; and the chamber having also vertically-oriented guiding tracks connected to or integral with a rigid wall enclosing the motor; (v) an inner rack connected to the compression wall; the inner rack running generally vertically on a track when the compression wall moves; (vi) a holder connected to the rack through the flexible inner wall of the housing; the holder holding one of several different heads which may be interchangeably connected thereto; the head rising as the inner rack moves upwards; the holder also having extending from it generally rounded or elliptical teeth and gum guards that prevent the gums or teeth from coming into direct contact with any hard portions of the holders or heads; the guards being reusable and replaceable; (vii) a cog wheel interlocking with the inner rack and being moved by the inner rack; the axis around which the cog wheel rotated being parallel to the axis of the gum arch; (viii) an outer rack moved by the cog wheel; the outer rack moving in the same plane as that of the inner rack but in the opposite direction; the outer rack being formed so that on its downwards motion it will cover and thereby cut off the water jet; (ix) a spring compressed by the upwards motion of the compression wall; the spring driving the compression wall downwards when the water jet is cut off; thereby moving the inner rack in a downwards direction and hence the attached holders and heads, thereby completing one generally vertical reciprocating cycle of the heads; (x) a lower secondary exhaust bellows chamber situated below the upper secondary exhaust bellows chamber and separated from it by the compression wall, and communicating with it by means of a one-way valve opening generally downwards, and also having an opening on the bottom of the lower chamber such that as the compression wall moves downwards, secondary exhaust fluids and exhaust substances are expelled out this opening and, by means of a tube or channel, out of portals on the outer surface of the housing; the upper secondary exhaust bellows chamber also having on its top surface a one-way valve which generally opens downwards for the entrance of the secondary exhaust fluids and exhausted substances into the upper chamber when the compression wall is driven downwards and suction or partial vacuum created in the upper chamber opens the one-way valve; (xi) lower exit holes in the floor of the motor to allow drainage or expulsion of water sprayed from the water jet; and (xii) a tube, pipe, or channel to the head from fresh water supplying the water jet; the fresh water to be continuously available to the head.

It is also an object to provide such a device in which the heads are comprised at least of interchangeable; (a) brushing heads, with bristles; the brushing heads being lubricated by the fresh water described, and being replaceable when, for example, worn or damaged; (b) polishing heads, with directional bristles on rotating disks to brush and irrigate or polish and irrigate the teeth or gums at differing angles; the disks being driven by part of the fresh water and the bristles being lubricated by the water also; some of the disks rotating in opposite directions; the disks with attached bristles being capable of being replaced individually when worn, and of being replaced individually by filler plugs or disks at places where no bristles are desired; and (c) irrigating (pulsating) and syringing (non-pulsating) heads, with directional nozzles to spray water at the teeth and gums at differing angles; the water spray being non-pulsating unless rendered pulsating by the intervention of a rotating interrupter inside the irrigating heads; the irrigating water being supplied by the fresh water described; the nozzles and disks being capable of being replaced by filler plugs at points where no water spraying is desired.

It is also an object to provide for such an apparatus in which there is also a controller, being an automatic device connectable to any faucet, having means to monitor the duration of use of the housing, and water temperature and pressure; the controller having also a diverter switch on a fresh water supply tube connecting the controller to the housing, to divert water from the faucet to the housing.

It is also an object to provide for such an apparatus with (i) automatic pre-set or user-set fresh water temperature control; (ii) automatic pre-set or user-set fresh water pressure control; (iii) automatic pre-set or user-set timer for shut-off of fresh water supplied to prevent injury or discomfort from excessive use of the housing;

(iv) automatic safety shut-off for fresh water temperatures or fresh water pressures above or below certain pre-set or user-definable points to prevent user discomfort or injury; (vi) a hose to supply fresh water to the housing; and (vii) a hose to return used water from the housing and expel it near the faucet into a sink, bathtub or other receptacle.

It is also an object to provide for such an apparatus in which more than one housing can be used simultaneously from one controller; the controller having separate temperature, pressure, and timer controls and separate hoses and diverter switch and safety shut-offs for each housing.

It is also an object to provide for such an apparatus in which there is also a connector, being a device similar to the controller but primarily intended to be used as a secondary, alternative, or flexible portable unit also with the controller; the connector being connectable to any faucet or, optionally, other water source, to control, and optionally monitor, the flow of fresh water to the housing.

It is also an object to provide for such an apparatus in which an additional purpose of the apparatus is to provide discouragement of thumb-sucking, and, optionally, protection of the teeth and gums, and in which the interchangeable heads also include cushioning heads; the cushioning heads to have a soft cushioning portion resting against the teeth and gums.

It is also an object to provide for such an apparatus in which a purpose of the apparatus is to provide protection of the teeth and gums, and, optionally, provides discouragement of thumb-sucking, and in which the motors are optionally replaced by cushioning material; and in which that portion of the housing inside the gum arch, being on the side of the gum arch contiguous to the tongue, has been removed, and, optionally, replaced with a semi-rigid biting member protruding between the teeth.

It is also an object to provide for such an apparatus in which the backmost portion of the housing is a flexible and durable material and functions as an elastic positioning lock, to hold the housing steadily in position contiguous to and, in conjunction with the flexible teeth and gum guard(s), a predetermined distance from teeth and gums while in use in the mouth or outside the mouth of any user, thereby rendering the apparatus usable by people with braces, crowns, implants, non-removable bridgework, false teeth or removable bridgework.

It is also an object to provide for such an apparatus in which the housing can be safely stored when not in use on any faucet by means of a clip or other suitable attachment means, thereby obviating the need for counter, cabinet, shelf, or other storage space.

Finally, it is also an object to provide for such an apparatus in which there are struts connecting the inner rack with the underside of the compression wall to ensure that the wall remains durable and rigid in both the generally upward and downward movements.

DETAILED DESCRIPTION OF THE INVENTION

Figure 1:
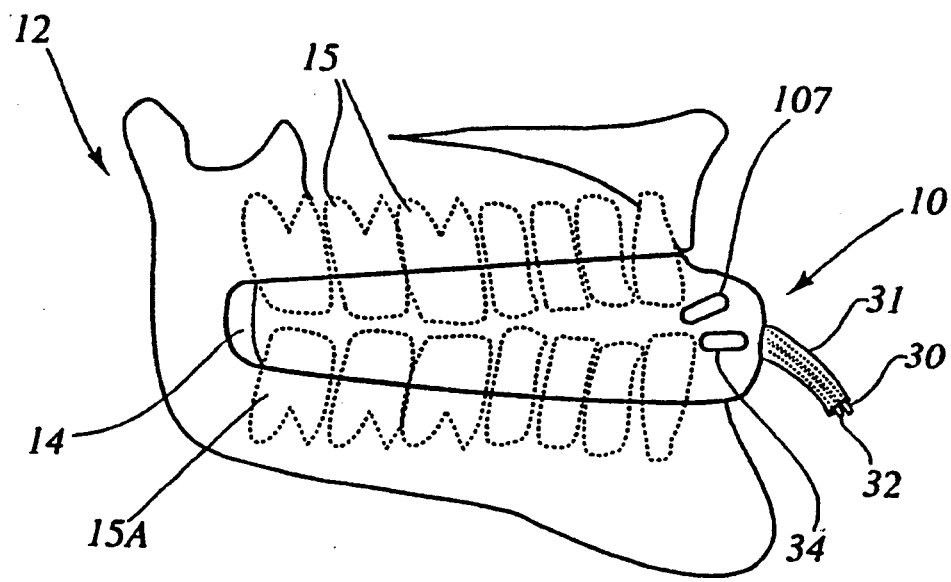
Figure 2:
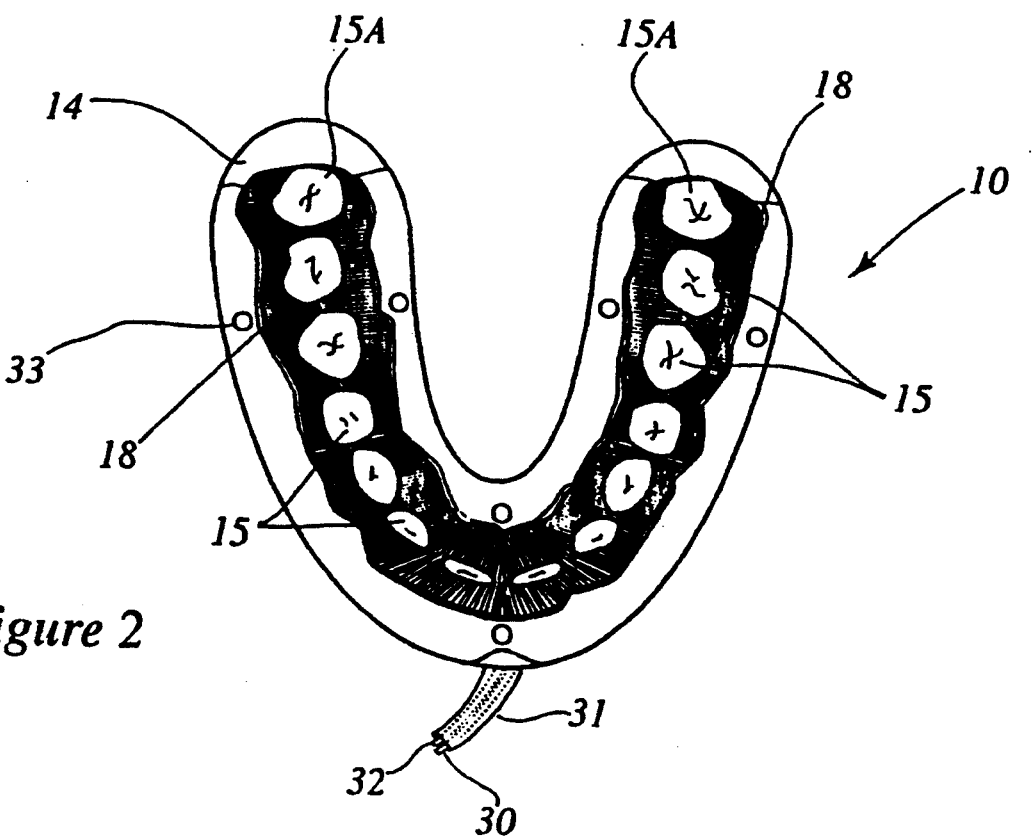
Figure 5:
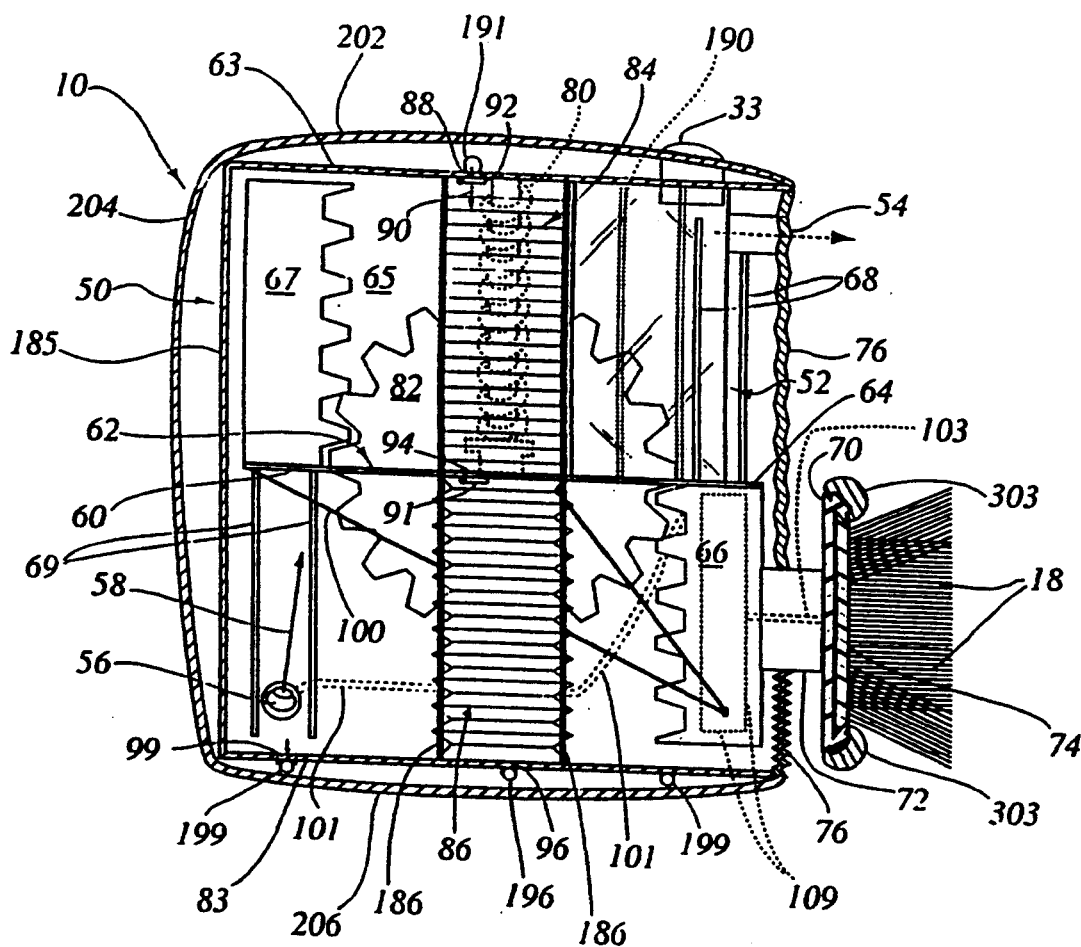
Figure 5A:
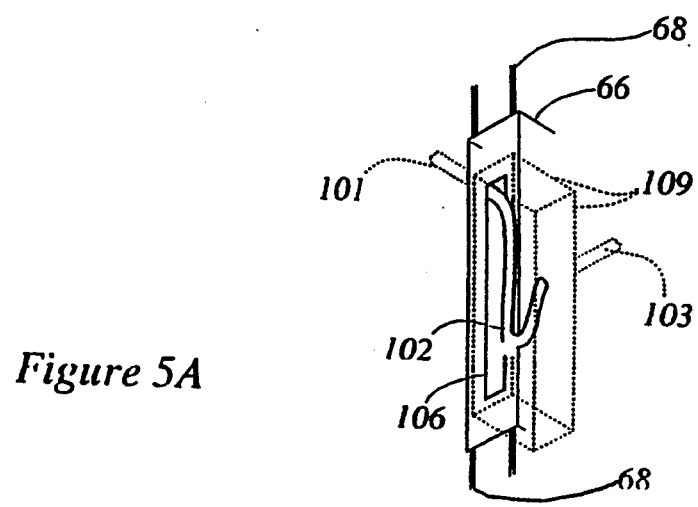
Figure 6:
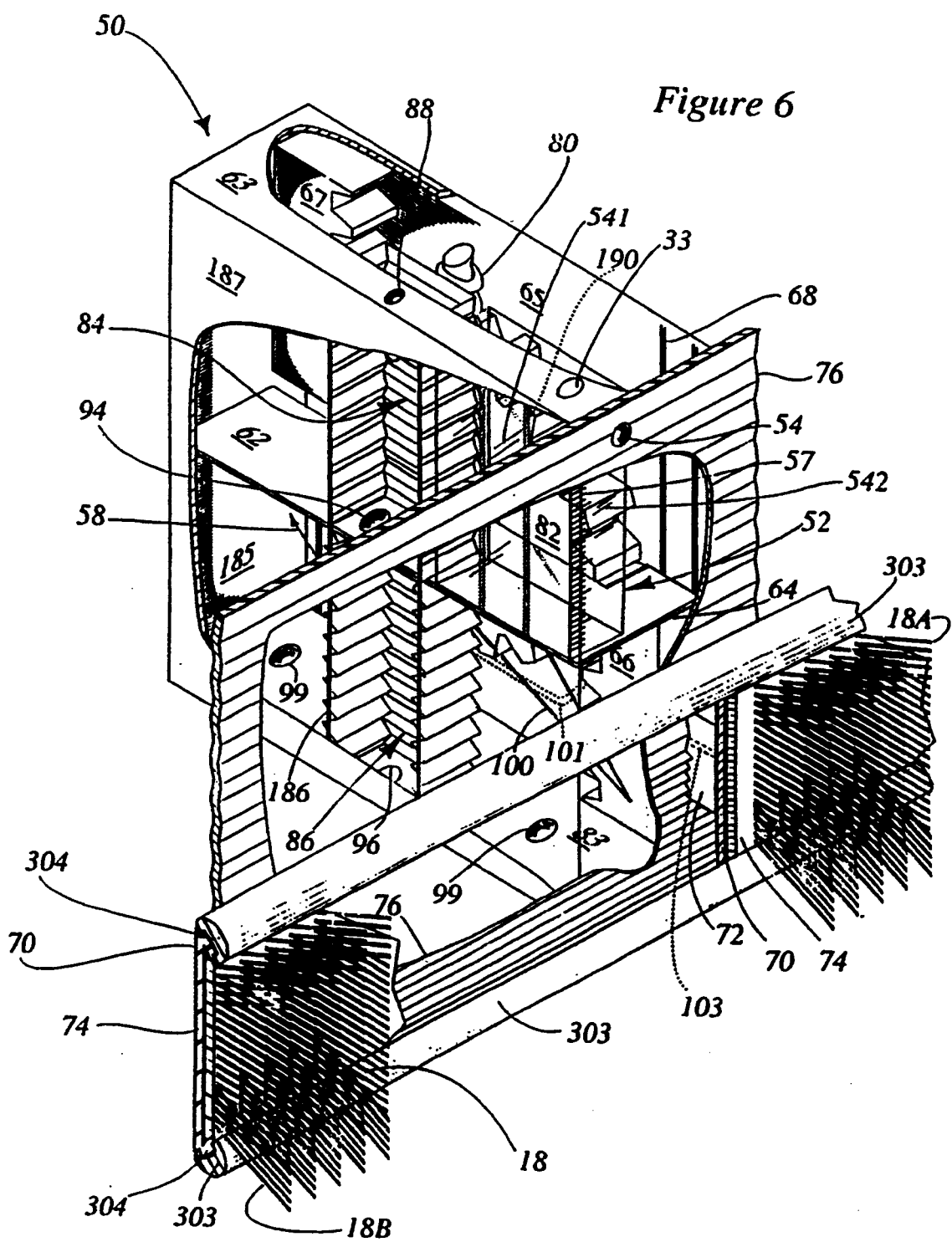
Figure 7:
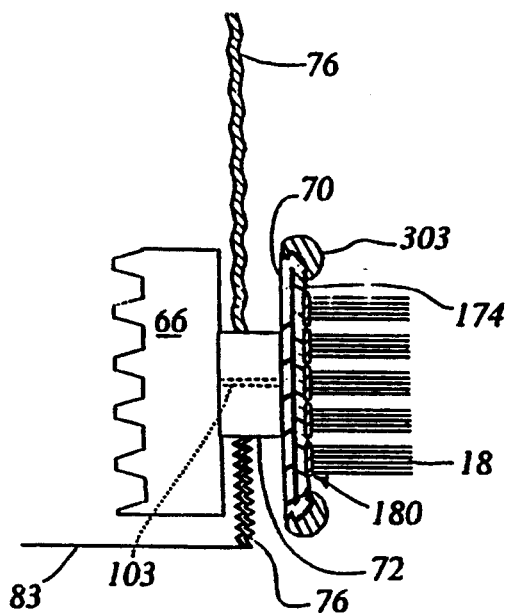
Figure 7A:
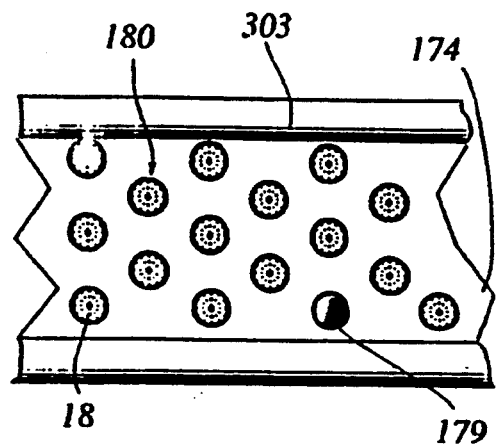
Figure 7B:
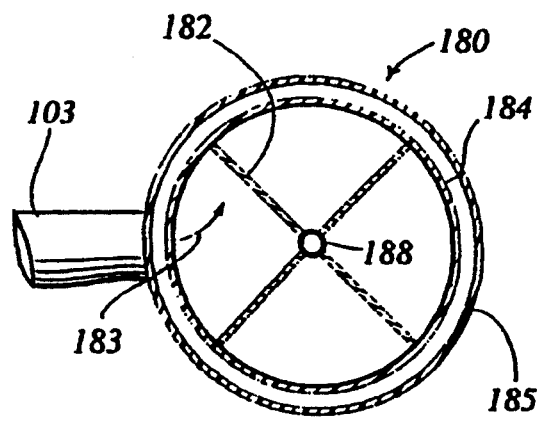
Figure 7C:
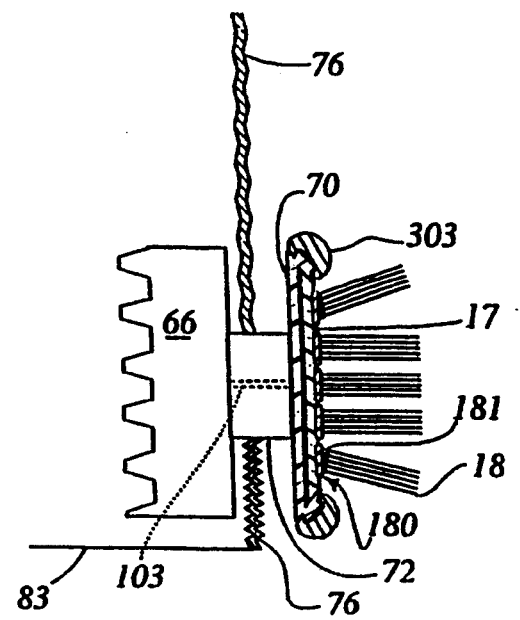
Figure 9:
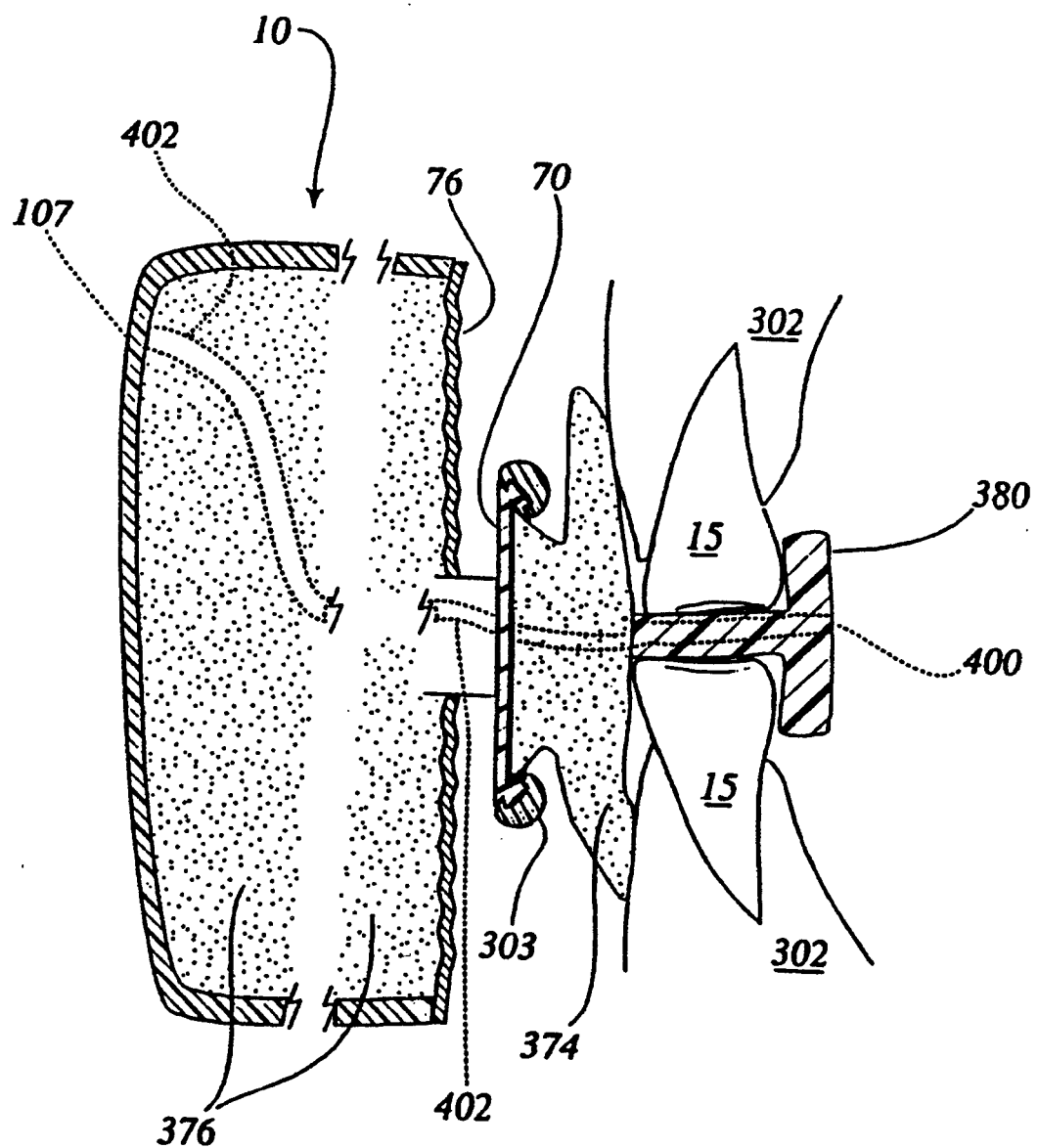

For this description, refer to the following diagrams, wherein like numerals refer to like parts:

FIG. 1, the invented device in place in a mouth, side elevation;

FIG. 2, first embodiment of the device, brushes in place contiguous to teeth of a lower jaw, plan view;

FIG. 3, first embodiment, brushes in perspective rear view;

FIG. 4, first embodiment, brushes perspective rear view with faucet controller;

FIG. 4A, portable faucet connector for the invented device, side elevation;

FIG. 5, first embodiment, enlarged view of brush and interior of motor in housing, side elevation section;

FIG. 5A, interior of inner rack, perspective cut-away view;

FIG. 6, first embodiment, enlarged view of brush and interior of motor without housing, perspective cut-away view;

FIG. 7, second embodiment, generally perpendicular polishing and brushing head and housing wall, side elevation section;

FIG. 7A, second embodiment, polishing and brushing head, front elevation;

FIG. 7B, second embodiment, detail of polishing and brushing head disk, front elevation section;

FIG. 7C, second embodiment, generally perpendicular and acute angle polishing and brushing head and housing wall, side elevation section;

FIG. 8, third embodiment, irrigating heads and housing walls with teeth side elevation section;

FIG. 8A, third embodiment, irrigating and syringing head, front elevation;

FIG. 8B, third embodiment, detail of irrigating and syringing head showing irrigating disk, front elevation section; and FIG. 9, fourth embodiment, cushioning head and housing, with teeth; side elevation section.

Referring to FIG. 1, mouth care device generally indicated as 10 can be seen in position in mouth of wearer generally indicated as 12. Backmost portion 14 of device 10 is of an elastic material that allows it to fit snugly over backmost teeth 15A. seen most clearly on FIG. 2, and thus hold firmly in place and contiguous to all teeth and gums. As seen in FIG. 2, teeth 15, including backmost teeth 15A, are pushed against from either side by brushes/bristles 18, which project out from the device at a generally perpendicular or acute angle to the gum arch. This can be seen more clearly in FIGS. 3 and 5. These brush bristles 18 move in a reciprocating vertical motion along the sides, bottoms and tops of all teeth, driven by clean water from a water supply such as a faucet, which enters device 10 through flexible pipe 30 inside flexible carrying hose 31 (seen in FIGS. 1-4). Most of this water, now called primary exhaust water, exits through flexible pipe 32, as will be explained in more detail later when the workings of the water motor 50 are provided (in FIGS. 5 and 6).

The water to drive the device 10 comes from faucet 40, as seen on FIGS. 4 and 4A. In the preferred embodiment, exemplified by FIG. 4, a water flow controller 42 is attached to a faucet 40. The controller contains means which allow settings for duration of use as with a timer 49, diverter switches 20 to select use mode, and monitoring of water temperature by gauge(s) or display(s) 47, water pressure by gauge(s) or display(s) 46, and time-remaining by timer(s) 49, as well as automatic safety shut-off(s) when pre-set (default) or user-set usage time(s) is (are) reached or in the event of unusually high or low water pressure or water temperature for each of one or more devices 10. Such controllers are known and commercially available. Fresh water diverter switch 20 on each hose 31 (only one hose 31 connecting one device 10 is shown) permits one or more users to monitor and control the direction of the flow of water from faucet 40 to hole 48 or to one or more devices 10 after the desired water temperature and water pressure have been selected by the user(s) at any faucet 40 and as monitored by the user(s) on controller 42. The generally up/down or in/out position of diverter switch 20 also indicates which device or devices 10 are in use and receiving fresh water from faucet 40. Also available will be a flexible portable connector 44, as in FIG. 4A, so that the device or devices 10 can be used while travelling and hook up to any faucet 40. Safety lock 45 on hose 31 attached to controller 42 or connector 44 will automatically pop hose 31 off said controller or connector, or turn off generally push-pull diverter switch 20, or employ such other means as to redirect fresh water flow from faucet 40 to hole 48 if the water temperature or water pressure are too high or too low or duration of use is too long, so as to protect a user's gums, teeth and mouth from discomfort or injury or improper use of device(s) 10. Safety lock 45 on hose 31 also allows the user to easily attach device(s) 10 to or detach device(s) 10 from controller 42 or connector 44. (Safety lock 45 is not shown on controller 42).

From both controller 42 and portable connector 44, primary exhaust of water used to drive brushes 18 leaves through hole 48, which in both cases is the end point of tube 32 as seen in FIG. 3. Hole 48 also allows clean water from faucet 40 to flow directly into a sink, shower, bathtub or other area or receptacle when said water is not diverted to one or more devices 10.

After use, all outer surfaces, breathing channels and hoses, and dispenser(s) of any device 10 can be cleaned by placing device 10 with portal(s) 33 open under running clean water from faucet 40. All other parts of device 10 are automatically self-cleaned simply by running device 10 from faucet 40 while not in the mouth. (This operation is not diagrammed.)

Secondary exhaust fluids shown by arrows 38 on FIG. 3, being used mouth fluids and suspended solids of a mixture of saliva, paste, mouthwash, polish, water, or the like, and perhaps blood, seen entering secondary exhaust fluid entry portals 36 on FIG. 3, are transported through the device 10 by the force of motors 50 and are expelled through secondary exhaust exterior exit portals 34, as seen on FIGS. 1, 3, and 4.

One or more devices 10 are attached by their respective hoses 31 to controller 42 or connector 44. (Only one such connection is shown diagrammatically.)

When not in use, device(s) 10 and their respective, self-coiling or retractable hoses 31 store on or in retaining clips 24 or the like on adjustable faucet strap(s) 22 or the like shown on FIG. 4. Other means of attachment or storage will suggest themselves to those familiar with the art.

Position of motors 50, in this example six in number but this number may be more or less, is shown by the dotted lines 200 in FIG. 3. Above each motor is a watertight entry portal 33 where paste, polish, mouthwash, or the like, can be put into the motor 50, said substances to be expelled onto all teeth 15 and 15A and amongst the brushes 18. The operation of this dispenser can be seen in more detail on FIGS. 5 and 6 where portal 33 leads to paste chamber generally indicated at 52 (which can also be used for polish, mouthwash, or the like). Paste chamber 52 is watertight, and is composed of flexible or elastic walls (shown transparent; seen best on FIG. 6). Front wall 541 of paste chamber 52, contiguous to rigid motor wall 187 seen in FIG. 6, is attached to and moves along chamber tracks 190, shown dotted in FIGS. 5 and 6, attached to or in wall 187. Thus chamber 52 can be vertically compressed to expel paste or the like through dispenser hole(s) 54. The mentioned transparency of paste chamber walls, such as inner side wall 542, and of device inner wall 76 (note that this wall 76 is shown as relatively opaque on FIG. 6, but is optionally transparent) facilitates: (1) user monitoring of chamber 52 contents (if any) prior to, during or after use of device(s) 10; (2) accurate user filling of portal 33 with desired amounts of desired fluids and substances by means of content indicator levels 57 on inner side wall 542; and (3) user monitoring of motor 50 and unit 10 cleanliness and operation during the cleaning operation (previously described).

The working of motor 50 is as follows: fresh water intake pipe 30 inside carrying hose 31 (shown on FIGS. 1, 2 and 3) attach to directional water jet nozzle 56, as seen in FIG. 5. Directional nozzle 56 emits a high speed water jet in direction of arrow 58 (seen also on FIG. 6); this jet of water hits the underside 60 of rigid and reciprocating compression wall generally indicated as 62, forcing it to rise upwards. Compression wall 62 is firmly connected to top 64 of inner rack 66, which therefore also rises, along tracks 68 attached to rigid back wall 65. Holder 70 is integrally connected by a vertically, movable bridge 72 to inner rack 66; thus brush head 74, and hence brushes 18, rise as rack 66 rises, to effect the basic upward brushing motion of the device, and at the same time cause coil spring 80 to be compressed. Note how inner wall 76 of device 10 encloses motor 50, and is flexible and, optionally, accordion-shaped; that is, wall 76 expands and contracts to accommodate the vertical movement of bridge 72 to which wall 76 is integrally connected; wall 76 is also flexible in the horizontal direction (as are holders 70, and brush heads 74; see FIGS. 2 and 3 to note how brushes 18 are flexed to fit into indentations between all teeth 15 and 15A).

The return brushing motion (not shown on the diagram) is accomplished as follows: as wall 62 rises, spring 80, running vertically between compression wall 62 and parallel rigid motor ceiling 63, is compressed. Simultaneously, outer rack 67, driven by cog wheel 82 attached to rigid motor back wall 65, has run down tracks 69 and completely covered nozzle 56, cutting off water jet 58. Thus with the upward pressure on wall 62 removed, compressed spring 80 is unopposed and urges wall 62 downwards, along with inner rack 66 and attached bridge 72, holder 70 and brush head 74. This accomplishes the downwards stroke of brushes 18.

Note also that brushes 18 are generally positioned perpendicular to the teeth and gum arch (teeth and gums not shown in FIGS. 5 and 6) but are also positioned diagonally downwards at the bottom and diagonally upwards at the top of brush head 74 at an acute angle to the teeth and gum arch relative to device 10 to ensure brushing above and below the gum lines as well as all tooth surfaces in between. On FIG. 6, diagonal top and bottom brushes are numbered as 18A and 18B respectively.

Also driven by this explained action of motor 50 is upper bellows chamber generally indicated at 84, and lower bellows chamber as 86, both of which move along bellows tracks 186 firmly attached to rigid front wall 187 (seen on FIG. 6) of motor 50. Secondary exhaust fluids and substances enter portals 36 on FIG. 3 and, with reference to FIG. 5, are carried by flexible tube(s) 191 to portal 88 in rigid ceiling 63 of motor 50 in direction of arrow 90. The vacuum created by upper bellows 84 when driven by motor 50 sucks in secondary exhaust fluids and suspended solids and the like through now open one-way valve 92. These fluids and substances fall (by gravity action) or are pushed, by upward movement of compression wall 62, through hole 94 in wall 62 into lower bellows chamber 86 through second downwards-opening one-way valve 91, and fall (by gravity action) or are pushed out of chamber 86 (by downward movement of compression wall 62) through lower exit hole 96). Tube(s) 196 will convey the secondary exhaust to exterior exhaust portal(s) 34 as shown on FIG. 1. Primary exhaust fluids and substances exit through flanking lower exits 99 and into tubes 199, and hence into pipe 32 seen on FIGS. 1, 2, and 3, to flow into a sink, bathtub, or other receptacle at faucet 40 through hole 48, as seen on FIGS. 4 and 4A. Primary and secondary exhaust holes 99 and 96 are located in rigid floor 83 of motor 50. As seen in FIG. 6, floor 83 is connected to rigid ceiling 63 by rigid side walls 65, 185 and 187, and flexible device 10 inner wall 76. These walls enclose and make watertight motor 50. Soft and flexible top, side and bottom walls 202, 204, and 206, respectively, and flexible tooth- and gum-side inner wall 76, as seen in FIG. 5, and elastic backmost portion 14, seen on FIGS. 1, 2 and 3, together comprise the housing of device 10.

Referring again to FIGS. 5 and 6, struts 100 help stabilize upwards and downwards motion of wall 62; they firmly connect lower side 60 or wall 62 to inner rack 66.

Clean water from faucet 40, arriving as described at nozzle 56 to power motor 50, also moves along channel or tube 101, located within or attached to rigid back wall 65 of motor 50, into tube 102 (seen in FIG. 5A) flexing freely inside cavity defined by surfaces 109 inside rack 66, (these surfaces 109 are shown dotted in FIG. 5, and best seen as enlarged view FIG. 5A). The water then flows from tube 102 into channel or tube 103 and into holder 70 and thence, in this embodiment, through brush head 74 and into brushes 18 for fresh water lubrication of all teeth and gums (not shown in FIGS. 5, 5A or 6). Note that this movement of fresh water is not stopped by interruption of water jet 58 by reciprocating movement of rack 67, since tube or channel 101 feeds off fresh water pipe 30 (not shown) supplying nozzle 56. Thus tube 102 and connecting channel or tube 103 move with rack 66, and, as rack 66 rises and falls along tracks 68, fresh water from stationary channel or tube 101 continuously enters reciprocating tube 102 through lengthwise opening 106 in rack 66, as seen in FIG. 5A.

During use, breathing through the device 10 is accomplished as follows: rear breathing holes numbered on FIG. 3 as 105 lead through tubes (not shown) in the flexible backmost portion 14 of device 10 and around to front breathing holes 107, best seen on FIG. 1. (Note that primary and secondary exhaust and fresh water tubes, not shown, inside the inner portion of the device, that is, the side facing the tongue, also follow this path around backmost portion(s) 14).

Other embodiments are as follows: in the second, shown in FIGS. 7, 7A, 7B and 7C, brush head 74 has been replaced with polishing head 174, which carries an array of brushes 18 on small rotating disks, generally indicated as 180. As shown in section detail FIG. 7B, these disks are made to rotate by water entering from channel or tube 103 and pushing vanes 182, here shown four in number. Note that water intake, here indicated by arrow 183, can be arranged to have some disks rotate clockwise and some counter-clockwise. This embodiment will be most useful for polishing and cleaning the teeth. Fresh water lubrication is accomplished through hole 188, supplying water generally through the center of each disk 180 of bristles 18. Note also that inner disk head 184 is removable from outer disk head 185: inner disk head 184 easily pops out so that worn brushes 18 can be replaced with a new inner disk head 184 which pops in to outer disk head 185. Inner disk head 184 provides generally perpendicular (to gums and teeth) bristles 18 (shown on FIG. 7) for brushing and lubricating or polishing and lubricating above and below the gum lines and all tooth surfaces in between. In FIG. 7C, upper and lower inner disk heads 184 have been replaced by inner disk heads 181 which comprise acute angle (to gums and teeth) bristles 18 for brushing and lubricating above and below the upper and lower gum lines, respectively, and, with disk heads 184, all tooth surfaces in between. Note also that in place of inner disk heads 184 or 181 with bristles 18, outer disk head 185 can receive a pop-in inner disk head plug 179 (shown on FIG. 7A) comprising a generally soft or flexible cover with no bristles, to prevent brushing and water leakage from said head 185 and to also meet the unique dentition and gum needs of the user.

Thus by repositioning one, some or all of said generally pop-in and pop-out upper and lower inner disk heads 181 downwards or upwards, respectively, or sideways, or replacing them with disk heads 184 or disk head plugs 179, varied angles of bristles 18 can be provided for brushing and lubricating or polishing and lubricating all or selected teeth and gums (not all options are diagrammed; teeth and gums are not shown in all Figures).

In a third embodiment, brush head 74 has now been replaced by oral irrigating and oral syringe head 274, as seen in FIG. 8, containing irrigating and syringing disks generally indicated as 280. In FIG. 8B, water 300 enters through channel or tube 103, into watertight outer disk 281. Internal rotating interrupter 282, shown dotted, causes water 300 (as indicated in FIG. 8) streaming out through directional nozzles 284 to pulse, giving a pulsating oral irrigation action directed against teeth 15 and 15A (shown in FIGS. 1, 2 and 3) and gums 302. Pop-in and pop-out inner irrigating disk 286, shown in FIG. 8B with interruptor 282, is removable from outer disk 281 and is easily replaced with a pop-in and pop-out syringing inner disk 287 as seen in the center of FIG. 8A, with directional nozzles 284 but with no interruptor 282. Note that such a syringing disk 287 without rotating interruptor 282 will give a non-pulsating oral syringe action, and that pulsating oral irrigation and non-pulsating oral syringe action can be combined in head 274 to meet the unique dentition and gum needs of the user, as shown in FIG. 8A.

Both front irrigating and syringing head 274 and back irrigating and syringing head 275 are shown in FIG. 8; the reader is reminded that this is the actual operating arrangement with both earlier embodiments as well, although only one side was diagrammed in each earlier case. Pop-in and pop-out plug covers 285 as seen on FIG. 8B can also be inserted into or removed from directional nozzles 284 to prevent water (whether pulsating or non-pulsating) from flowing or leaking from nozzles 284 and to also meet the unique dentition and gum needs of the user; or an entire inner plug disk 288, with no nozzles, as seen in FIG. 8A, could be inserted. In this third embodiment, soft of flexible teeth and gum guards 303, while existing in earlier embodiments, become most important since no bristles 18 exist to keep device 10 a predetermined distance away from teeth 15 and gums 302, as seen on FIG. 8. Note also that vertical size of head 274 combined with up and down vertical run of reciprocating motion of head 274 must be calculated and formed so that teeth and gum guard 303 at no time rises high enough or falls low enough to enter space between teeth 15; otherwise hard surface of head 274 might strike and chip tooth edge 316. Optionally, where available materials permit, head 274 can be formed of a flexible or soft surface. Gum and teeth guards 303 generally pop on and pop off or slide onto and slide off of holder 70 in all embodiments for ease of replacement; gum and teeth guards 303 are also available in various sizes and configurations to meet the unique dentition and gum needs of the user. For additional teeth and gum protection, other flexible or soft or like materials can be affixed to or used in the construction of the surfaces of device 10 exposed to mouth, gum or tooth surfaces, including holder 70, heads 74, 174, and 274, and their other exposed components (to the mouth, gums or teeth) like rotating disks 180 and directional nozzles 284. Surfaces of device 10 exposed to the mouth, gums or teeth, like said disks 180 and nozzles 284, can be recessed below or placed flush with the surface of heads 174 and 274, respectively. (These options are not diagrammed).

In all of these three embodiments, gum and teeth guards 303 also help to position device 10 and wall 76 a safe and uniform distance from all teeth 15 and gums 302, and permit the effective brushing, cleaning, lubricating, massaging, and polishing of all teeth and gums by device 10; this positioning is best seen on FIG. 8.

A fourth and final embodiment is as a mouth protector and anti-thumb-sucking device. One possible example is diagrammed in FIG. 9; primary teeth and gum cushion 374 is slid into holder 70; secondary teeth and gum cushion 376 may replace motor 50 in device 10, as shown; teeth 15 bite down on integral semi-rigid biting member 380; air is breathed in from and exhausted to front breathing holes 107 from rear breathing holes 400 through channel(s) or tube(s) 402 in member 380, cushioning piece 374 and optional cushion 376. In this first variant, for use as a mouth protector, as illustrated in FIG. 9, the device 10 is constituted so that it has no back segment. Optionally in a second variant (not diagrammed), primarily for use as an anti-thumbsucking device, the entire device 10 exists as described in the first three embodiments, without secondary cushion 376, and the cushioning piece(s) such as 374 in FIG. 9 is/are merely slid into holder(s) 70 as described for other attachments previously described. The biting member 380 is optional in this variant, and can be attached to cushion 374.

Thus the reader is reminded that in all four embodiments the attachments previously described are interchangeable and can be easily and quickly slid into or attached to holder 70 or removed or slid out of holder 70, with backmost portion(s) 14 holding the device 10 in position for the first three embodiments and the second variant of the fourth. In the first variant of the fourth embodiment, the device is held in place by the clamping of teeth 15 on biting member 380, as shown in FIG. 9.

It should be noted that alternative variations of or attachments to or embodiments of the invention are possible. Numerous alterations of the structures herein disclosed will suggest themselves to those skilled in the art. It is to be understood that the present disclosure relates to preferred embodiments of the invention which are for the purposes of illustration only and are not to be construed as a limitation of the invention.

I claim:

1. An apparatus for automatic and simultaneous caring for the teeth and gums; said caring comprising brushing, cleaning, lubricating, massaging, oral irrigating, oral syringing, and polishing; said apparatus comprising:
   (a) a housing of flexible material, formed to follow the shape of a gum arch and fit the teeth; said housing having:
      (i) a top having holes therein;
      (ii) flexible, expandable and compressible inner walls facing the teeth and gum, and flexible soft surfaces on all external portions of said housing which come into contact with mouth, teeth or gums;
      (iii) channels or tubes through the housing to automatically conduct breathing air in and out of the mouth and exhaust fluids and exhaust substances out of the mouth, said exhaust fluids and exhaust substances comprising used paste, polish, mouthwash, saliva, water, blood and the like;
      (iv) watertight covers on, or within, the holes in the top surface of the housing; said holes being for the introduction of paste, polish, mouthwash, or the like into compressible paste chambers inside the housing;
      (v) one or more water-driven motors inside said housing having portals open to said teeth and to the channels or tubes in said housing;
      (vi) a bellows or vacuum chamber inside each motor to automatically suction exhaust fluids and exhaust substances away from the teeth and gums, and a compression wall movable to automatically propel exhaust fluids through said channels or tubes and exhaust substances out of said housing;
      (vii) a paste chamber inside each motor; said paste chamber being cyclically compressed by the compression wall and so automatically supplying paste, polish, mouthwash or the like to the teeth and gums through a dispenser hole or holes in a housing inner wall;
      (viii) a vertically reciprocatable bridge linkage connected to each motor through a housing inner wall; the bridge integrally connected to a holder external to the housing; said holder having a head removeably attached thereto; said head moving up and down vertically with said linkage;
      (ix) means to connect the housing to a faucet to provide a flow of fresh water to the housing; and
      (x) means to monitor the fresh water temperature and pressure and duration of flow of water into the housing.

2. An apparatus as in claim 1, in which the housing or some part thereof is formed of transparent material.

3. An apparatus as in claim 1, where the watertight covers are mounted to pop-up when opened.

4. An apparatus as in claim 1, in which the bridge linkage is integrally connected to a reciprocating rack in each motor.

5. An apparatus as in claim 1, in which the means to connect the apparatus to a faucet to provide a flow of fresh water to the housing and the means to monitor water temperature and pressure and duration of the flow of water into the housing are accomplished by a controller; the controller being an automatic device connectable to any faucet; said controller having a diverter switch on a fresh water supply tube connecting the controller to the housing, to divert water from the faucet to the housing or to a sink, bathtub, or other receptacle.

6. An apparatus as in claim 5, in which more than one of said housings can be simultaneously used with the controller, and in which the temperature, pressure and duration of water flowing to each housing can be adjusted independently.

7. An apparatus as in claim 1, in which more than one of said housings can be simultaneously from said source of fresh water.

8. An apparatus as in claim 1, which also includes user-set of pre-set automatic control of duration of the flow of water into the housing.

9. An apparatus as in claim 1, which also includes means to automatically shut off the flow of water to the housing when pre-determined maximum water temperature or pressure or duration of flow of water into the housing are reached.

10. An apparatus as in claim 1, in which the means to connect the apparatus to a faucet to provide a flow of fresh water to the housing is accomplished by a flexible portable connector running from the housing, which can be connected to any faucet, thereby rendering the apparatus portable; said connector allowing the user to control the direction of the flow of fresh water from any faucet to said housing or to a sink, bathtub or other receptacle, and, optionally, providing means for monitoring water temperature and water pressure to said housing, or means for selecting the duration of use of said housing.

11. An apparatus as in claim 10, in which more than one of said housings can be attached to the connector and can be used simultaneously from said flow of fresh water.

* * * * *

UNITED STATES PATENT AND TRADEMARK OFFICE
CERTIFICATE OF CORRECTION

PATENT NO. : 5,365,624
DATED : November 22, 1994
INVENTOR(S) : Michael S. Berns

It is certified that error appears in the above-identified patent and that said Letters Patent is hereby corrected as shown below:

Title Page, [76] Inventor: replace address as follows:

--1311 Kilborn Avenue, Ottawa, Ontario, Canada K1H 6L2--

Signed and Sealed this

Twenty-first Day of February, 1995

Attest:

BRUCE LEHMAN

Attesting Officer   Commissioner of Patents and Trademarks